United States Patent
Bevirt et al.

(10) Patent No.: US 6,739,448 B1
(45) Date of Patent: May 25, 2004

(54) METHOD AND APPARATUS FOR SHUTTLING MICROTITRE PLATES

(75) Inventors: JoeBen Bevirt, Emerald Hills, CA (US); Gabriel Noah Brinton, Palo Alto, CA (US)

(73) Assignee: Incyte Corporation, Palo Alto, CA (US)

( * ) Notice: Subject to any disclaimer, the term of this patent is extended or adjusted under 35 U.S.C. 154(b) by 257 days.

(21) Appl. No.: 09/496,220

(22) Filed: Feb. 1, 2000

(51) Int. Cl.[7] .............................................. B65G 25/00
(52) U.S. Cl. ................................ 198/750.12; 198/468.8
(58) Field of Search ........................... 198/468.8, 468.4, 198/465.1, 750.12, 773, 775; 414/225.01, 752.1, 749.1

(56) References Cited

U.S. PATENT DOCUMENTS

| | | | |
|---|---|---|---|
| 3,934,702 A | 1/1976 | Snyder et al. ................. 198/20 |
| 4,077,444 A | 3/1978 | Gilson et al. ................ 141/130 |
| 4,478,094 A | 10/1984 | Salomaa et al. ......... 73/863.32 |
| 4,483,927 A | 11/1984 | Takekawa ..................... 436/43 |
| 4,558,984 A * | 12/1985 | Garrett ........................ 198/775 |
| 4,582,990 A | 4/1986 | Stevens ....................... 250/328 |
| 4,681,742 A | 7/1987 | Johnson et al. .............. 422/102 |
| 5,004,399 A * | 4/1991 | Sullivan et al. ......... 414/225.01 |
| 5,102,623 A | 4/1992 | Yamamoto et al. ............ 422/63 |
| 5,122,342 A | 6/1992 | McCulloch et al. ........... 422/65 |
| 5,203,445 A * | 4/1993 | Shiraiwa ................... 198/465.1 |
| 5,226,462 A | 7/1993 | Carl ............................... 141/1 |
| 5,245,530 A | 9/1993 | Taki ....................... 364/167.01 |
| 5,309,959 A | 5/1994 | Shaw et al. .................. 141/130 |
| 5,356,525 A | 10/1994 | Goodale et al. ............. 204/299 |
| 5,811,306 A | 9/1998 | Komatsu ...................... 436/54 |
| 5,865,224 A | 2/1999 | Ally et al. ................... 141/130 |
| 5,988,236 A | 11/1999 | Fawcett ....................... 141/130 |
| 6,063,579 A | 5/2000 | Bevirt et al. .................... 435/6 |
| 6,148,878 A | 11/2000 | Ganz et al. ................. 141/129 |

FOREIGN PATENT DOCUMENTS

| | | |
|---|---|---|
| EP | 292995 | 11/1988 |
| EP | 301583 | 2/1989 |
| EP | 351988 | 1/1990 |
| WO | WO92/12233 | 7/1992 |
| WO | WO99/15905 | 4/1999 |

OTHER PUBLICATIONS

CCS Packard, "Robotic Systems for Laboratory Automation", dated May 2, 2000.

* cited by examiner

Primary Examiner—Joseph E. Valenza
(74) Attorney, Agent, or Firm—Incyte Corporation

(57) ABSTRACT

A shuttle apparatus for transferring sample carriers comprising a shuttle table having a mating section, the mating section allowing a sample carrier to be transferred between the shuttle table and a mating support structure. The shuttle table can optionally further comprise a mating section having a void section.

14 Claims, 7 Drawing Sheets

METHOD AND APPARATUS FOR SHUTTLING MICROTITRE PLATES

FIELD OF THE INVENTION

The present invention relates to the transfer of sample carriers. In particular, the present invention relates to an apparatus for transferring sample carriers and a method for presenting and retrieving sample carriers.

DESCRIPTION OF RELATED ART

In the modem laboratory, numerous experiments are performed daily. Hence, large numbers of samples are handled and processed. To comply with the increasing safety and quality standards in the industry, extreme care is required in handling these samples. Therefore, process automation in sample handling has become common in the modem laboratory.

In performing experiments, sample carriers are usually employed. Sample carriers allow for more than one sample to be processed at a time. An example of a sample carrier is the microwell plate, also known as the microtitre plate. Microwell plates are plastic plates that contain a uniformly-standard ninety-six microwells. Other sizes are also commercially available.

Microwell plates are usually stacked in one location. A transfer mechanism removes the microwell plates from the stack and takes them to the desired processing area. After the microwell plate has been processed, the transfer mechanism takes the microwell plates to a further processing area or to another stacking area for storage.

The automated handling of numerous sample carriers has presented serious difficulties. When transferring the microwell plates from stacking areas to the processing areas, it is often necessary to transfer the microwell plates without a cover. Alternatively, if covered plates are used, the need often arises to remove the microwell cover during the transfer. However, the transfer mechanisms usually handle the sides or top of the microwell plates. Therefore, the cover is not fully accessible, and the microwell plates cannot be transferred without a cover. For removal of the cover for processing, the cover must be removed by grasping the sides or corners of the cover. Another problem with transferring the microwell plates is the inability to access the plate from both sides.

Further drawbacks of the prior art include transferring the microwell plates without firmly securing the plates to the transfer mechanism. During transfer, insecure support increases the likelihood of the samples being spilled or damaged, which leads to inaccurate testing results.

With the advent of process automation in the modern laboratory, there is a need for a transfer mechanism that handles only the bottom side of sample carriers and never handles the sides or top of the carrier. Further, there is a need for firmly securing the sample carriers to the transfer mechanism. In addition, there is a need for a transfer mechanism that can move a microwell plate from one storage area to another storage area.

SUMMARY OF THE INVENTION

The present invention concerns a shuttle apparatus for transferring sample carriers comprising a shuttle table having a mating section, the mating section allowing a sample carrier to be transferred between the shuttle table and a mating support structure. In an embodiment, the shuttle table has at least one vacuum apparatus. In another embodiment, the shuttle table has at least one boss structure. Optionally, the surfaces of the boss structures can be chamfered.

In a further embodiment, the shuttle table comprises at least one vacuum apparatus and boss structure. Further, the boss structures can be chamfered.

In an additional embodiment, the shuttle table has at least one gripper apparatus. In another embodiment, the shuttle table has at least one gripper apparatus and boss structure. Optionally, the boss structures can be chamfered.

In a further embodiment, the mating section further comprises a void section. Optionally, the void is C-shaped, which allows clearance for a mating support structure. In another embodiment, the shuttle apparatus further comprises a rotary device, with the rotary device attachable to the shuttle arm.

Another aspect of the invention is a method of retrieving and presenting a sample carrier with a shuttle apparatus comprising the steps of: (a) presenting a sample carrier to a shuttle table of the shuttle apparatus from a mating support structure; (b) engaging the bottom surface of the sample carrier with the shuttle table; (c) moving the shuttle apparatus; and (d) presenting the sample carrier to a mating support structure.

The method of retrieving and presenting a sample carrier with a shuttle apparatus can optionally further comprise allowing the mating support structure to pass through the shuttle table, with the mating support structure passing through a void of the shuttle table. In addition, when presenting the sample carrier to the mating support structure, the invention can optionally further comprise allowing the mating support structure to pass through the shuttle table, with the mating support structure passing through a void of the shuttle table.

The method of presenting the sample carrier to the shuttle table can optionally further comprise allowing the shuttle table to pass through the mating support structure, with the shuttle table passing through a void of the mating support structure. In addition, when presenting the sample carrier to the mating support structure, the invention can optionally further comprise allowing the shuttle table to pass through the mating support structure, with the shuttle table passing through a void of the mating support structure.

The method of retrieving and presenting a sample carrier with a shuttle apparatus can further comprise securing the sample carrier to the shuttle table. Securing the sample carrier can further comprise registering the sample carrier by boss structures on the surface of the shuttle table, with the boss structures engaging the sides of the sample carrier. Further, registering the sample carrier with the boss structures can optionally comprise chamfering the boss structures, thereby allowing for any misalignment of the sample carrier with the shuttle table. Securing the sample carrier can further comprise pulling a vacuum on the sample carrier with a vacuum apparatus located on the shuttle table. Optionally, securing the sample carrier can comprise (a) registering the sample carrier by a series of boss structures on the surface of the shuttle table, with the boss structures engaging the sides of the sample carrier; (b) chamfering the boss structures, thereby allowing for any misalignment of the sample carrier with the shuttle table; and (c) pulling a vacuum on the sample carrier with a vacuum apparatus located on the shuttle table.

The method of securing the sample carrier can optionally further comprise engaging the sample carrier with a gripper apparatus, with the gripper apparatus located on the shuttle table. Optionally, securing the sample carrier can comprise (a) registering the sample carrier by a series of boss structures on the surface of the shuttle table, with the boss structures engaging the sides of the sample carrier; (b) chamfering the boss structures, thereby allowing for any misalignment of the sample carrier with the shuttle table; and (c) engaging the sample carrier with a gripper apparatus, with the gripper apparatus located on the shuttle table.

The method of retrieving and presenting a sample carrier with a shuttle apparatus can optionally further comprise rotating the shuttle apparatus horizontally about a central, vertical axis.

The method of moving the shuttle apparatus can further comprise moving in a linear direction or angular direction in a horizontal plane. Optionally, the shuttle apparatus can be moved in a vertical plane. An additional option includes moving the shuttle apparatus in a vertical and a horizontal plane. Further, the step of moving the shuttle apparatus can optionally further comprise moving the sample carrier without a cover. In addition, moving the shuttle apparatus can optionally further comprise removing a cover from the sample carrier. The optional step of removing a cover from the sample carrier can further comprise removing the cover by only engaging the top of the cover. In addition, removing the cover by only engaging the top of the cover can further comprise engaging the sample carrier with a pneumatically-actuated arm having vacuum cups.

The method of retrieving and presenting a sample carrier with a shuttle apparatus can further comprise an improved conveyor system having the steps of: (a) integrating a series of shuttle apparatuses with multiple mating support structures, with the shuttle apparatuses incrementally transferring sample carriers to each mating support structure; (b) synchronizing presentation of the sample carriers to the mating support structures, and (c) moving the shuttle apparatuses between the mating support structures, with the shuttle apparatuses moving in the linear or angular direction.

The present invention also concerns a shuttle apparatus for transferring sample carriers comprising: (a) a shuttle table; (b) a shuttle arm, with the shuttle arm supporting the shuttle table; (c) the shuttle table having a C-shaped void section, thereby allowing clearance for a mating support structure and presentation of a sample carrier; (d) the shuttle table having a top surface and a bottom surface; (e) the top surface of the shuttle table having two vacuum apparatuses and a series of boss structures, with the boss structures having chamfered surfaces; (f) each vacuum apparatus comprising two vacuum chucks and a flat surface running between the vacuum chucks; (g) each vacuum apparatus located on opposite sides of the C-shaped void section; (h) the shuttle table having hollow channels running from the vacuum apparatus and exiting the shuttle table through an opening at the back side of the shuttle table; and (i) a rotary device attached to the shuttle arm.

The present invention also concerns a shuttle apparatus for transferring sample carriers comprising: (a) a shuttle table; (b) a shuttle arm, with the shuttle arm supporting the shuttle table; (c) the shuttle table having a C-shaped void section, thereby allowing clearance for a mating support structure and presentation of a sample carrier; (d) the shuttle table having a top surface and a bottom surface; (e) the top surface of the shuttle table having a gripper apparatus and a series of boss structures, with the boss structures having chamfered surfaces; (f) the gripper apparatus comprising a pneumatic actuator and a gripper arm; and (i) a rotary device attached to the shuttle arm.

The present invention also concerns a means for retrieving and presenting a means for carrying samples comprising: (a) presenting the means for carrying samples to a means for transferring the samples; (b) a means for only engaging the bottom surface of the means for carrying samples; (c) a means for moving the means for retrieving and presenting; (d) a means for securing the means for carrying samples to the means for retrieving and presenting during transfer; and (e) a means for presenting the means for carrying samples from the means for retrieving and presenting to a means for receiving.

Further, the present invention concerns a method of retrieving and presenting a sample carrier with a shuttle apparatus comprising the steps of: (a) presenting a sample carrier to a shuttle table of the shuttle apparatus from a first mating support structure; (b) allowing the first mating support structure to pass through the shuttle table, the first mating support structure passing through a void of the shuttle table; (c) engaging the bottom surface of the sample carrier with the shuttle table; (d) moving the shuttle apparatus along a horizontal plane; (e) removing a cover from the sample carrier, the sample carrier movable without a cover; (f) removing the cover from the sample carrier comprising the step of engaging the top of the cover; (g) engaging the top of the sample carrier with a pneumatically-activated arm having vacuum cups; (h) securing the sample carrier to the shuttle table, securing the sample carrier to the shuttle table comprising the steps of (i) registering the sample carrier by boss structures on the surface of the shuttle table, the boss structures engaging the sides of the sample carrier; (ii) chamfering the boss structures, thereby allowing for any misalignment of the sample carrier with the shuttle table; and (iii) pulling a vacuum on the sample carrier with a vacuum apparatus, the vacuum apparatus located on the shuttle table; (i) rotating the shuttle apparatus horizontally about a central vertical axis; j) presenting the sample carrier to a second mating support structure; and (k) allowing the second mating support structure to pass through the shuttle table, the second mating support structure passing through a void of the shuttle table.

Additionally, the present invention concerns a method of retrieving and presenting a sample carrier with a shuttle apparatus comprising the steps of: (a) presenting a sample carrier to a shuttle table of the shuttle apparatus from a first mating support structure; (b) allowing the first mating support structure to pass through the shuttle table, the first mating support structure passing through a void of the shuttle table; (c) engaging the bottom surface of the sample carrier with the shuttle table; (d) moving the shuttle apparatus along a horizontal plane; (e) removing a cover from the sample carrier, the sample carrier movable without a cover; (f) removing the cover from the sample carrier comprising the step of engaging the top of the cover; (g) engaging the top of the sample carrier with a pneumatically-activated arm having vacuum cups; (h) securing the sample carrier to the shuttle table, securing the sample carrier to the shuttle table comprising the steps of (i) registering the sample carrier by boss structures on the surface of the shuttle table, the boss structures engaging the sides of the sample carrier; (ii) chamfering the boss structures, thereby allowing for any misalignment of the sample carrier with the shuttle table; and (iii) engaging the sample carrier with a gripper apparatus, with the gripper apparatus located on the shuttle table; (i) rotating the shuttle apparatus horizontally about a central vertical axis; (j) presenting the sample carrier to a second mating support structure; and (k) allowing the second mating support structure to pass through the shuttle table, the second mating support structure passing through a void of the shuttle table.

The present invention allows a sample carrier to be transferred between a shuttle apparatus and a mating support structure. An advantage of the present invention includes handling the bottom side of sample carriers, thereby allowing for easy access to the sample carrier. A further advantage of the present invention includes firmly securing the sample carriers to the transfer mechanism. The invention also allows the sample carrier to be transferred without a cover. In addition, the present invention allows for the transfer of sample carriers from a storage area to a process area or to another storage area.

DESCRIPTION OF ILLUSTRATIVE EMBODIMENTS

Figure 1:
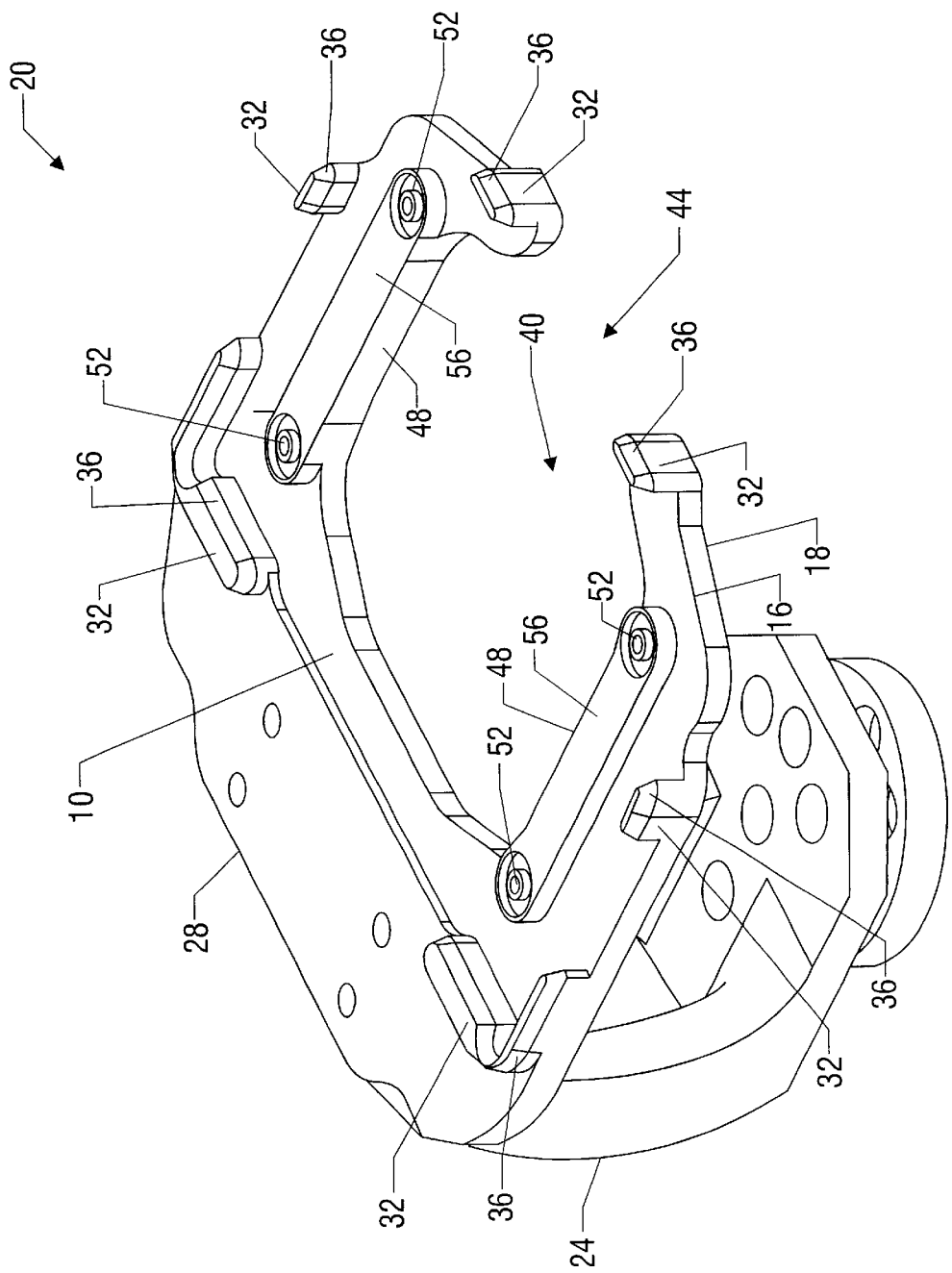
FIG. 1 illustrates one embodiment of a shuttle apparatus.

FIG. 1 shows one embodiment of the shuttle apparatus 20 comprising a shuttle arm 24 and a shuttle table 28. The shuttle arm 24 lies in a vertical plane, and the shuttle table 28 lies in a horizontal plane, with the shuttle arm 24 giving support to the shuttle table 28. The shuttle table 28 has a top surface 16 and a bottom surface 18. The top surface 16 of the shuttle table 28 having a mating section 10. In addition, the top surface 16 of the shuttle table 28 has a series of boss structures 32. The boss structures 32 are protuberances that rise from the top surface 16 of the shuttle table 28. As shown, the boss structures 32 are incrementally placed along the edges of the shuttle table 28. In some embodiments, the boss structures 32 are chamfered. The chamfers 36 located on the surface of the boss structures 32.

As illustrated, the mating section 10 of the shuttle table 28 contains a void. This void section 40 is a C-shaped cutout of the shuttle table 28. As shown, the open end 44 of the C-shaped cutout is located at the front end of the shuttle table 28, which allows entrance into the void section 40.

Also located on the top surface 16 of the shuttle table 28 are multiple vacuum apparatuses 48, which contain multiple vacuum chucks 52. Another attempt at providing such vacuum chucks 52 is disclosed in U.S. patent application Ser. No. 09/183,776 filed Oct. 30, 1998, which is entitled "Alignment Mechanism" by Bevirt, Brinton, and Lachenmeier and incorporated by reference in its entirety. FIG. 1 shows the shuttle apparatus 20 with a vacuum apparatus 48 on each side of the void section 40. Each vacuum apparatus 48 is shown having two vacuum chucks 52. Each vacuum chuck 52 is enclosed within a vacuum boss structure 56. The vacuum boss structure 56 protects the vacuum chucks 52. Further, the vacuum boss structure 56 provides a flat surface to engage the underside of a sample carrier, thereby allowing the vacuum chucks 52 to pull a proper vacuum. In one embodiment, the vacuum is pulled through a channel in the shuttle table 28. The channel runs longitudinally from the vacuum apparatus 48 to an opening at the back of the shuttle table 28. Preferably, an individual channel services each vacuum apparatus 48.

Figure 2:
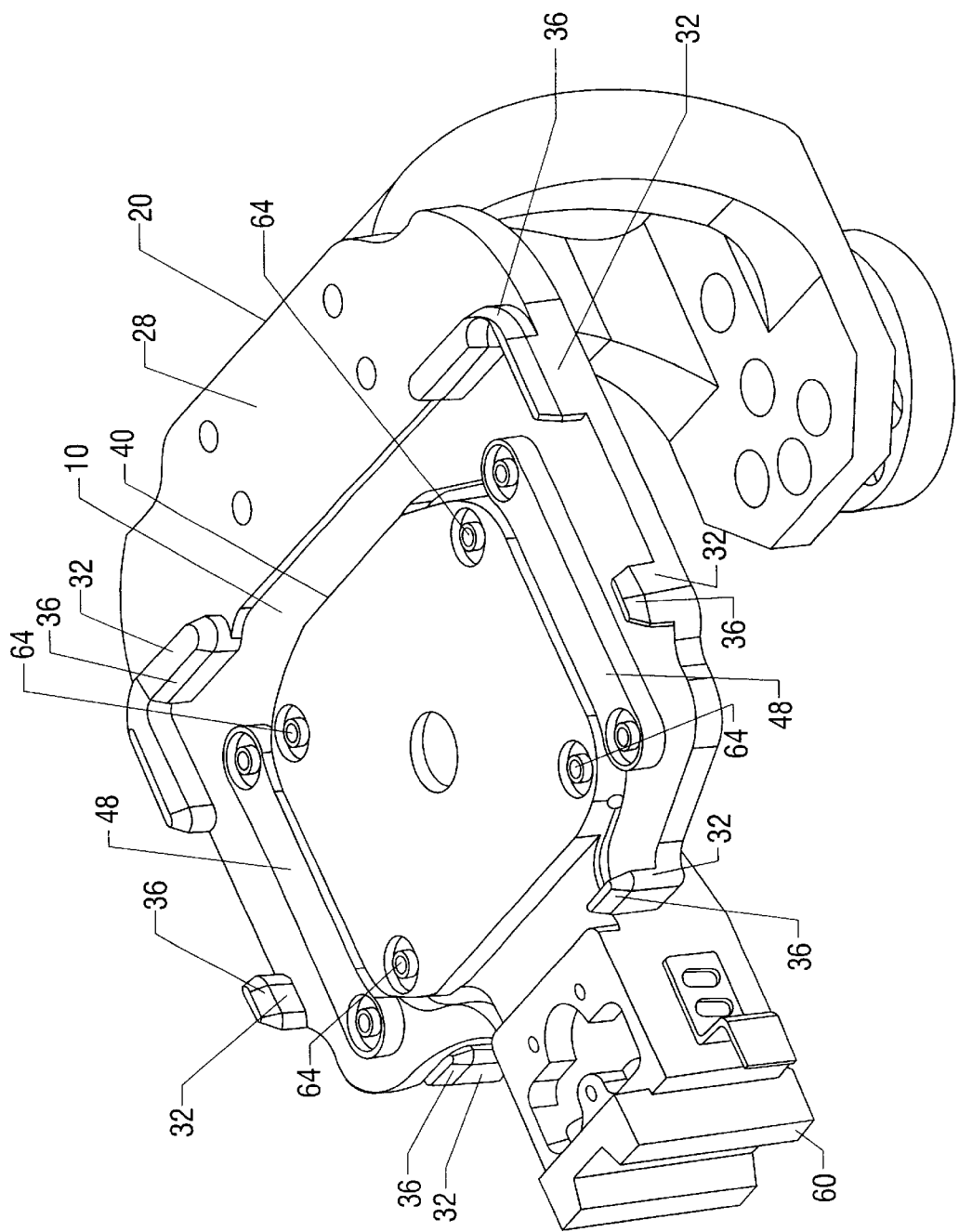
FIG. 2 illustrates an embodiment of the invention showing both a shuttle apparatus and a mating support structure.

FIG. 2 shows a shuttle apparatus 20 and a mating support structure 60. As shown, the mating support structure 60 passes within the void section 40 of the mating section 10. The shuttle apparatus 20 receives a sample carrier from the mating support structure 60. The sample carrier contains the experimental samples that are to be processed or transferred between storage areas. A variety of carriers well known to one skilled in the art may be used for the sample carrier of the present invention. Suitable examples of carriers include but are not limited to microwell plates and pipette tip boxes.

The mating support structure 60 operates in a vertical plane. When it is desired for the mating support structure 60 to retrieve a sample carrier, a raising means will raise the mating support structure 60 until the top surface of the mating support structure meets the bottom surface of the sample carrier. The mating support structure 60 will then lower itself and the sample carrier. As shown in FIG. 2, the mating support structure 60 will be aligned vertically with the void section 40 of the shuttle table 28. The mating support structure will continue downward passing from the top side 16 of the shuttle table 28, through the void section 40, and exiting the bottom side 18 of the shuttle table 28, thereby presenting the sample carrier to the shuttle apparatus 20. The top surface 16 of the shuttle table 28 meeting the bottom surface of the sample carrier. In an embodiment, the mating section 10 does not have a void section 40. Instead, the mating support structure 60 has a void section, thereby allowing the shuttle table 28 to pass through the void section of the mating support structure 60 during presentation of the sample carrier.

When the shuttle apparatus 20 receives the sample carrier, the boss structures 32 register the sample carrier. By engaging tightly with the sides of the sample carrier, the boss structures 32 secure the sample carrier to the shuttle apparatus 20. In case of misalignment between the shuttle apparatus 20 and the sample carrier, chamfers 36 are manufactured onto the boss structures 32, thereby beveling the surface of the boss structures 32. The sloped surface of the chamfers 36 allow a misaligned sample carrier to slide along the surface of the chamfers 36 and engage with the boss structures 32, thereby accounting for the misalignment.

As the boss structures 32 engage the sample carrier, the vacuum chucks 64 of the mating support structure 60 are turned off. Thus, the sample carrier disengages from the mating support structure 60 as it passes through the void section 40. When the vacuum chucks 64 of the mating support structure 60 are turned off, the vacuum apparatus 48 of the shuttle apparatus 20 is engaged, thereby firmly securing the sample carrier. A vacuum valve controls the vacuum pulled through the vacuum apparatus 48. Also, a vacuum sensor can be located with the vacuum valve. The vacuum sensor senses whether a vacuum is actually being pulled through the vacuum apparatus 48, thereby determining if a sample carrier is present on the shuttle table 28. A vacuum sensor can also be located on the mating support structure 60.

Figure 3:
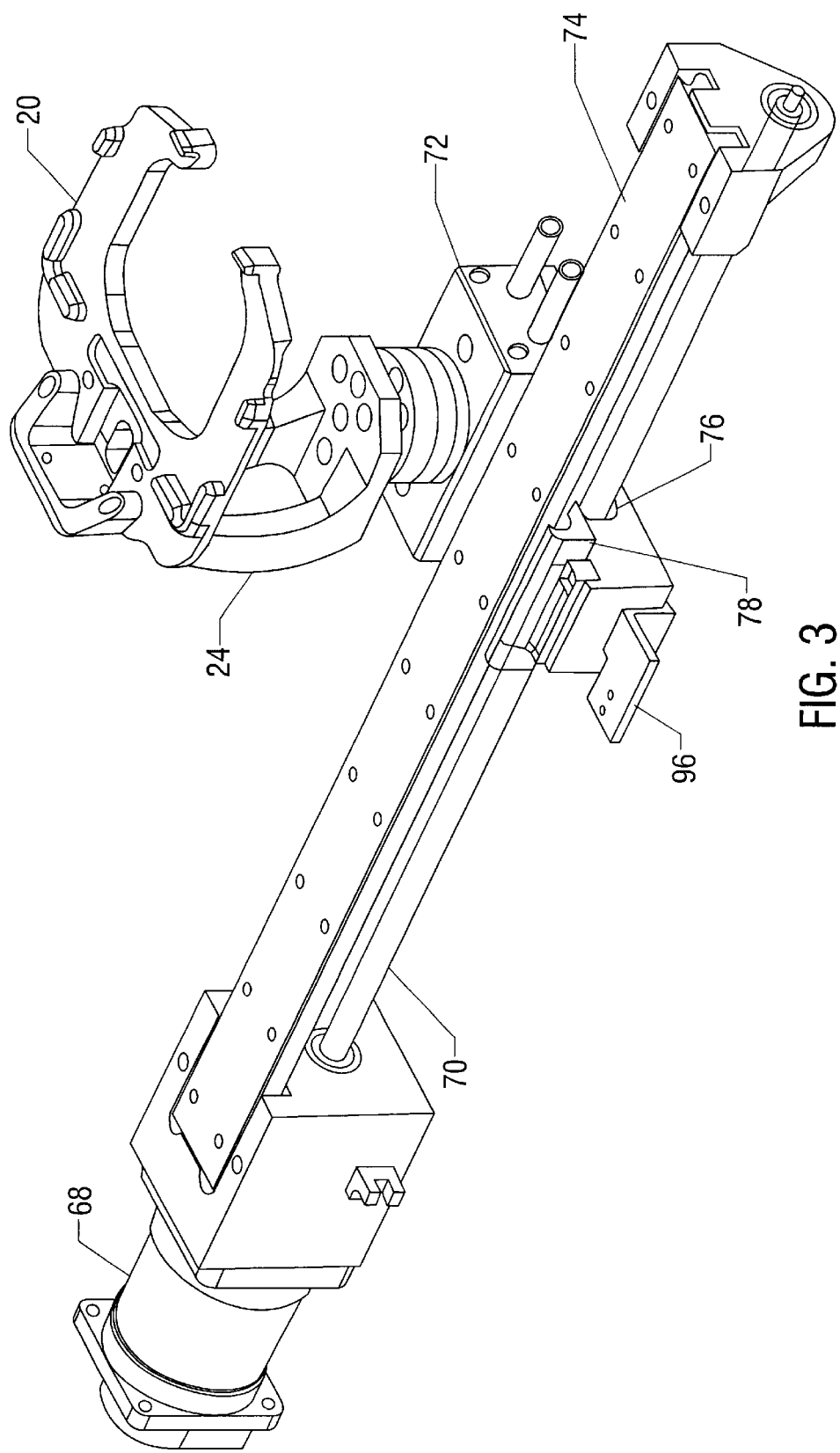
FIG. 3 illustrates an embodiment with the shuttle apparatus connected to a motorized ball screw and rotary device.

FIG. 3 shows the shuttle apparatus 20 attached to a rotary device 72 and a motorized ball screw 70. The ball screw 70 is attached to a motor 68, which is the motive force for the shuttle apparatus 20. The ball screw 70 is threaded through a ball screw nut 76, which is attached to a linear bearing block 78. A linear bearing 74 is attached to the linear bearing block 78. Also illustrated in FIG. 3 is a rotary device 72. As shown, the rotary device 72 is attached to the shuttle arm 24 and a rotary table bridge 96, which is fastened to the ball screw nut 76.

The rotary device 72 horizontally rotates the shuttle apparatus 20, allowing access to the sample carrier from both sides. A variety of rotary devices well known to one skilled in the art can be used to rotate the shuttle apparatus 20. Suitable examples of rotary devices useful for rotation include but are not limited to a pneumatic rotary actuator, an encoder/motor assembly, hydraulic rotac, and linear actuation of a linear-to-rotary linkage. In one embodiment, the rotary device 72 will rotate the shuttle apparatus 20 one hundred and eighty degrees.

The shuttle apparatus 20 is movable in a horizontal plane or a vertical plane. In the horizontal plane, the shuttle apparatus 20 is movable in either a linear direction or an angular direction. The shuttle apparatus 20 is further movable in both a vertical and a horizontal plane. A motive force will transfer the shuttle apparatus 20 between processing stations or storage areas. Many modes of transfer are well known to one skilled in the art. Appropriate modes of motive force for transferring the shuttle apparatus 20 include but are not limited to a motorized ball screw, rack and pinion, belt drive, chain drive, linear motor, pneumatic, and hydraulic.

FIG. 3 illustrates one embodiment of the invention in which the rotary device 72 and shuttle apparatus 20 are shuttled by a motorized ball screw 70. The motor 68 rotates the ball screw 70, which twists within the threads of the ball screw nut 76. The ball screw 70 twisting within the ball screw nut 76 causes the ball screw nut 76 to move, which in turn causes the attached linear bearing block 78 and rotary table bridge 96 to move. Movement of the rotary table bridge 96 in turn causes movement of the rotary device 72 and attached shuttle apparatus 20. The linear bearing block 78 moves along the linear bearing 74, thereby causing the shuttle apparatus 20 to move in a linearly horizontal direction.

Figure 4:
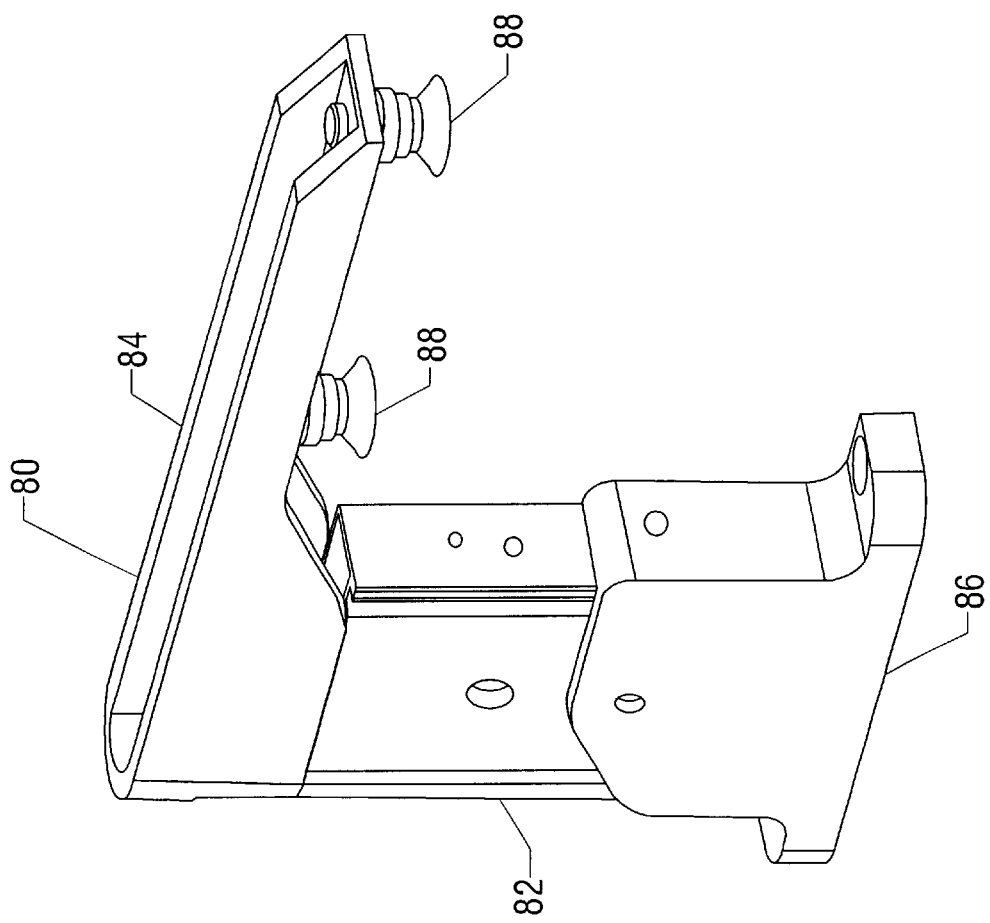
FIG. 4 illustrates an embodiment of a pneumatically-actuated arm.

FIG. 4 depicts a pneumatically-actuated arm 80. As shown, the pneumatically-actuated arm 80 comprises a pneumatic actuator 82, an arm 84, a base 86, and multiple vacuum cups 88. The base 86 provides support for the arm 84 and pneumatic actuator 82. The arm 84 is connected to the pneumatic actuator 82 at one end, with the other end hanging free. Vacuum cups 88 are located on the end of the arm 84 that is hanging free. The pneumatic actuator 82 provides the raising means for moving the arm 84 up and down.

When the sample carrier is transferred by the shuttle apparatus 20, only the bottom side of the sample carrier is engaged by the shuttle apparatus 20, thereby allowing the sample carrier to be transferred with or without a lid. The lid can be removed by a variety of means. For example, a lid can be removed by grippers grasping the sides or corners of the lid. An embodiment of the present invention implements the pneumatically-actuated arm 80 to remove the lid by engaging only the top of the lid.

In one embodiment, the pneumatically-actuated arm 80 is a separate structure from the shuttle apparatus 20. As the shuttle apparatus 20 transfers the sample carrier, the shuttle apparatus 20 passes underneath the cantilevered arm 84 of the pneumatically-actuated arm 80. The arm 84 is horizontally stationary but moves in the vertical plane. As the shuttle apparatus 20 moves under the arm 84, the arm 84 will lower until the vacuum cups 88 engage the top of the sample carrier lid. As the vacuum cups 88 engage the lid, a vacuum is pulled, thereby securing the lid to the vacuum cups 88. The pneumatic actuator 82 will then lift the arm 84 with the lid, allowing the shuttle apparatus 20 to transfer the sample carrier without the lid.

Figure 5:
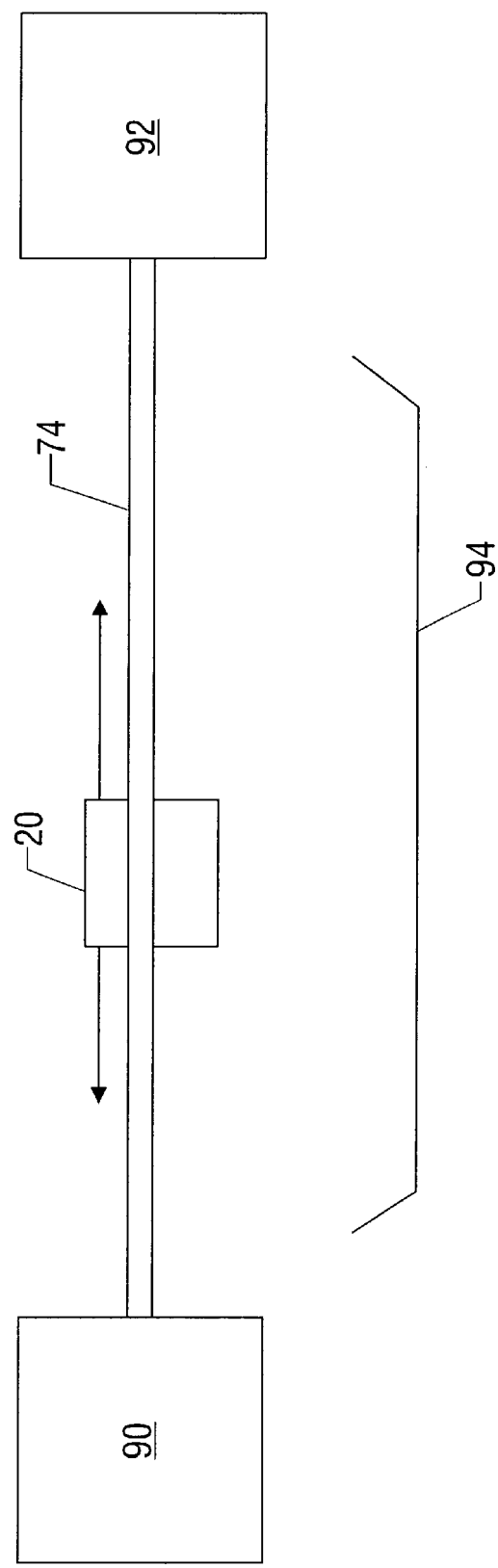
FIG. 5 is a schematic of a shuttle apparatus positioned between two stackers.

FIG. 5 illustrates a method of transferring a sample carrier between two stackers. As shown, a first stacker 90 and a second stacker 92 face each other. A process area 94 lies between the first stacker 90 and the second stacker 92. The shuttle apparatus 20 transfers a sample carrier along a linear bearing 74, which runs between the first stacker 90 and the second stacker 92.

In one embodiment, the shuttle apparatus 20 will retrieve a sample carrier from the first stacker 90. A motorized ball screw 70 will then move the shuttle apparatus 20 along a linear bearing 74. As the shuttle apparatus 20 moves away from the first stacker 90, a rotary device 72 will rotate the shuttle apparatus 20 one hundred eighty degrees, with the shuttle apparatus 20 still remaining in motion along the linear bearing 74. The shuttle apparatus 20 will then be guided by the linear bearing 74 through a process area 94. After the sample carrier is processed, the shuttle apparatus 20 will continue moving along the linear bearing 74 until reaching the second stacker 92. Upon reaching the second stacker 92, the shuttle apparatus 20 will present the sample carrier to a mating support structure 60 of the second stacker 92. Alternatively, the shuttle apparatus 20 can return the sample carrier to the first stacker 90.

Figure 6:
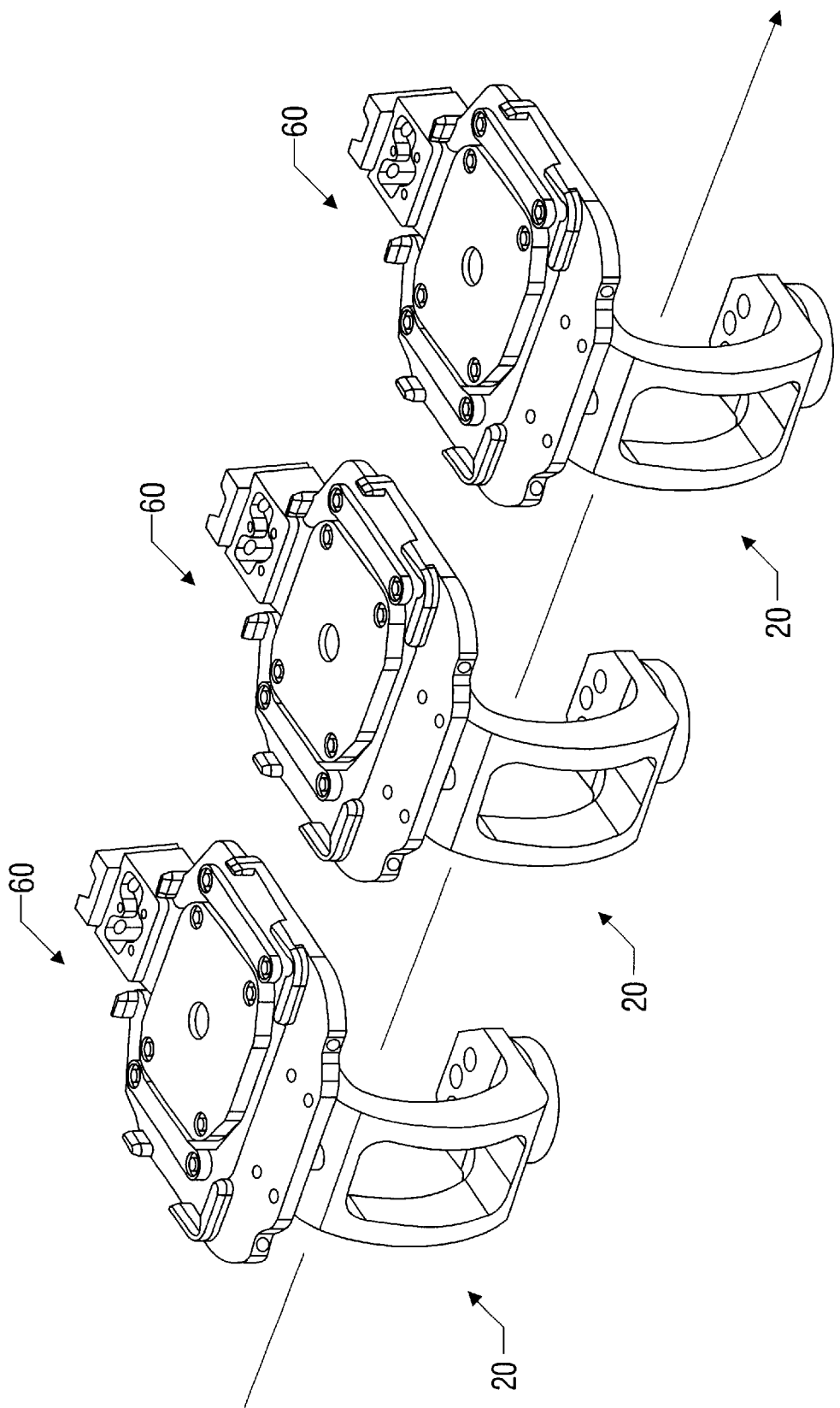
FIG. 6 illustrates an embodiment of an improved shuttle apparatus conveyor system.

FIG. 6 illustrates a method for an improved conveyor system. As shown, the method involves a series of shuttle apparatuses 20. The series of shuttle apparatuses 20 are integrated with a series of mating support structures 60. The mating support structures 60 are horizontally stationary but can move up or down. The shuttle apparatuses 20 are linearly or angularly movable in the horizontal direction. The shuttle apparatuses 20 transfer sample carriers between processing stations, incrementing each sample carrier from one processing station to the next processing station. Presentation of the sample carriers at each processing station is synchronized between the shuttle apparatuses 20. In an embodiment, the mating support structures 60 are horizontally stationary in a circular orientation. The shuttle apparatuses 20 incrementally transfer the sample carriers between the mating support structures 60 in a circular path, with the circular path of the shuttle apparatuses 20 concentric with the circular orientation of the mating support structures 60.

Figure 7:
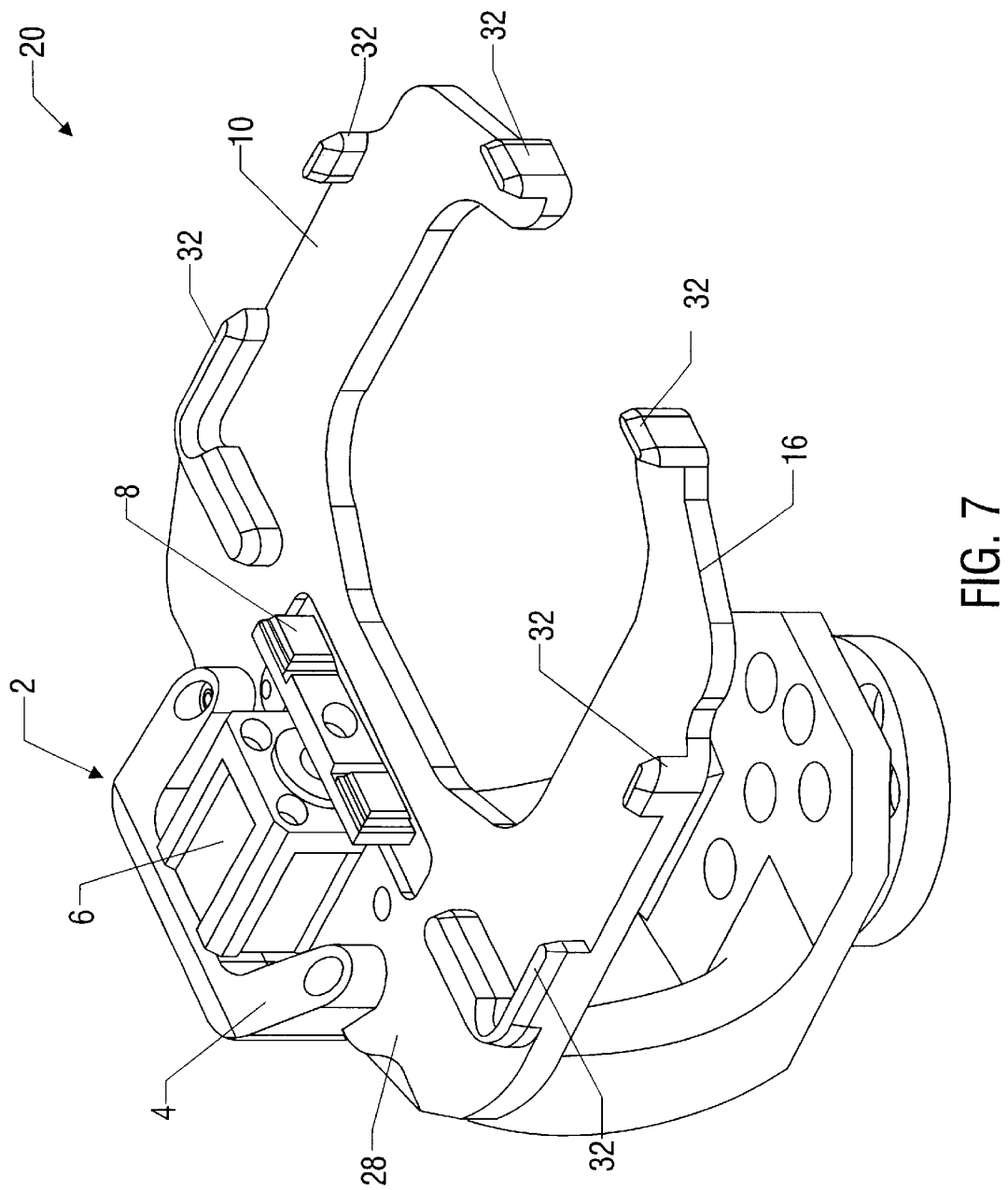
FIG. 7 illustrates an embodiment of the invention showing a gripper apparatus.

FIG. 7 illustrates another embodiment of the shuttle apparatus 20, whereby the sample carrier is secured by a gripper apparatus 2. As shown, the top surface 16 of the shuttle table 28 has a series of boss structures 32 and a gripper apparatus 2. The gripper apparatus 2 comprises a gripper base 4, which is attached to the shuttle table 28. A pneumatic actuator 6 is attached to the gripper base 4 and a gripper arm 8.

When a sample carrier is presented to the mating section 10 of the shuttle table 28, the boss structures 32 will engage the sample carrier. After the boss structures 32 engage the sample carrier, the pneumatic actuator 6 moves the gripper arm 8 horizontally across the top surface 16 of the shuttle table 28. The gripper base 4 provides horizontal support to the pneumatic actuator 6 as it moves the gripper arm 8. The gripper arm 8 will engage a side of the sample carrier, thereby firmly securing the sample carrier between the gripper arm 8 and the boss structures 32.

The preceding description of the illustrative embodiments of the present invention is not intended to be a complete list of every possible embodiment of the invention. Persons skilled in this field will recognize that modifications can be made to the specific embodiments described here that would be within the scope of the present invention.

What is claimed is:

1. A shuttle apparatus for transferring sample carriers, comprising:
 a shuttle table, the shuttle table having a mating section with a void, the mating section being adapted to receive a sample carrier; and
 a mating support structure having one degree of freedom adapted to travel vertically through the void in the mating section, thus transferring the sample carrier from the mating section to the mating support structure.

2. The apparatus according to claim 1, wherein the shuttle table has at least one vacuum apparatus.

3. The apparatus according to claim 2, wherein the shuttle table has at least one boss structure.

4. The apparatus according to claim 3, wherein said boss structures are chamfered.

5. The apparatus according to claim 1, wherein the shuttle table further comprises at least one vacuum apparatus and boss structure.

6. The apparatus according to claim 5, wherein said boss structures are chamfered.

7. The apparatus according to claim 1, wherein the void is C-shaped, which allows clearance for a mating support structure.

8. A method of retrieving and presenting a sample carrier with a shuttle apparatus comprising the steps of:
 presenting the sample carrier to a shuttle table of the shuttle apparatus from a mating support structure having one degree of freedom;
 engaging the bottom surface of the sample carrier with the shuttle table;
 moving the shuttle apparatus; and
 presenting the sample carrier to the mating support structure, wherein the presenting of the sample carrier to the shuttle table further comprises allowing the mating support structure to pass through the shuttle table, the mating support structure passing through a void of the shuttle table to transfer the sample carrier.

9. The method of claim 8, wherein the presenting of the sample carrier to the mating support structure further comprises allowing the mating support structure to pass through the shuttle table, the mating support structure passing through a void of the shuttle table to transfer the sample carrier.

10. The method of claim 8, further comprising the step of securing the sample carrier to the shuttle table.

11. The method of claim 10, wherein securing the sample carrier further comprises registering the sample carrier by boss structures on the surface of the shuttle table, the boss structures engaging the sides of the sample carrier.

12. The method of claim 11, wherein registering the sample carrier with the boss structures further comprises chamfering the boss structures, thereby allowing for any misalignment of the sample carrier with the shuttle table.

13. The method of claim 10, wherein securing the sample carrier further comprises pulling a vacuum on the sample carrier with a vacuum apparatus, the vacuum apparatus located on the shuttle table.

14. The method of claim 10, wherein securing the sample carrier further comprises registering the sample carrier by a series of boss structures on the surface of the shuttle table, the boss structures engaging the sides of the sample carrier, chamfering the boss structures thereby allowing for any misalignment of sample carrier with the shuttle table; and pulling a vacuum on the sample carrier with a vacuum apparatus, the vacuum apparatus located on the shuttle table.

* * * * *